United States Patent
Goll et al.

Patent Number: 5,947,902
Date of Patent: Sep. 7, 1999

[54] APPARATUS AND METHOD FOR CALIBRATION OF AN ULTRASOUND TRANSMISSION PROBE

[75] Inventors: Jeffrey H. Goll, Oswego; Joe P. Buhler, Portland, both of Oreg.

[73] Assignee: Metra Biosystems, Inc., Mountain View, Calif.

[21] Appl. No.: 09/150,914

[22] Filed: Sep. 10, 1998

Related U.S. Application Data

[63] Continuation-in-part of application No. 08/938,101, Sep. 26, 1997
[60] Provisional application No. 60/026,815, Sep. 27, 1996.
[51] Int. Cl.$^6$ ..................................................... A61B 8/00
[52] U.S. Cl. ........................................................... 600/442
[58] Field of Search ...................... 600/437, 438, 600/442; 607/122

[56] References Cited

U.S. PATENT DOCUMENTS

| | | | |
|---|---|---|---|
| 5,042,489 | 8/1991 | Wiener et al. | 600/449 |
| 5,480,422 | 1/1996 | Ben-Haim | 607/122 |

OTHER PUBLICATIONS

Laugier et al., Ultrasound Images of the Os Calcis: a New Method of Assessment of Bone Status, Proceedings IEEE 1993 Ultrasonics Symposium, vol. 2, pp. 989–992, Oct. 31, 1993.

*Primary Examiner*—George Manuel
*Assistant Examiner*—Ali M. Imam
*Attorney, Agent, or Firm*—Bromberg & Sunstein LLP

[57] ABSTRACT

An apparatus and methods for determining a measure equivalent to broadband sound attenuation from transient or other measures derived from acoustic signals propagated through bone and, additionally, for using this measure for the calibration of an ultrasound bone analysis instrument. A synthetic mathematical filter corresponding to a given value of broadband ultrasound attenuation is applied to the signal propagated through a calibration of known or neutral acoustic properties. The value of the acoustic measure corresponding to the resultant waveform is determined and associated with the broadband ultrasound attenuation value corresponding to the synthetic mathematical filter. A model relating the acoustic measure to BUA values may thereby be established for subsequent clinical application.

11 Claims, 9 Drawing Sheets

APPARATUS AND METHOD FOR CALIBRATION OF AN ULTRASOUND TRANSMISSION PROBE

The present application is a continuation-in-part of U.S. application No. 08/938,101, filed Sep. 26, 1997 (the "Prior Application"), and claims priority from U.S. provisional application number 60/026,815, filed Sep. 27, 1996, both of which applications are herein incorporated by reference.

TECHNICAL FIELD

The present invention relates to an apparatus and methods for the acoustic analysis of bone, and more particularly to an apparatus and methods for converting acoustic measures including transient acoustic measures to equivalent Broadband Ultrasound Attenuation (BUA) measures and for calibrating measurements of a particular measurement unit in terms of equivalent BUA measures.

BACKGROUND ART

Various methods for measurement of bone characteristics using acoustic techniques are known for identifying patients in need of treatment for bone conditions and diseases. Many acoustic techniques utilize a first (transmitting) transducer to provide an acoustic signal, typically at ultrasonic frequencies, to the subject from a first external location and a second (receiving) transducer at a second external location disposed on the opposite side of the bone of interest to receive the signal transmitted by the first transducer through the bone and intervening soft tissue. (The transducers are typically coupled to the subject through a suitable fluid, such as water or water gel.)

One often-quoted acoustic characteristic of bone is the so-called Broadband Ultrasound Attenuation (BUA), typically quoted for the frequency range of approximately 300 to 700 kHz The BUA is defined as the slope of a linear logarithmic-amplitude versus frequency plot of the energy transmitted through the heel. BUA measures are typically performed by Fourier transforming the signal produced in the receiving transducer due to transmission of a broadband acoustic pulse through the bone undergoing measurement. The Fourier components of the received signal are typically ratioed to the corresponding components measured through a medium of known or assumed spectral attenuation characteristics so that the slope of the bone attenuation versus frequency may be derived. Bone is known to have the effect of preferentially attenuating higher frequencies—this preferential attenuation is known to decrease as the bone becomes increasingly porous, thus the BUA similarly decreases for more porous bone. BUA measurements typically suffer from several drawbacks, including contamination of the received signal by acoustic transmission between the transmitting and receiving acoustic transducers via multiple paths through the bone. For example, the BUA result for a given measurement may depend not only on the apparatus used but on the length and portion of the time domain record used, the type, if any, of window function used with the data, the frequency range and method used for estimation of the slope, and the methods used for calibration.

The early portion of the received waveform may be more representative of the measured body part, as discussed in greater detail in the description below. It is desirable, moreover, to convert measurements made with respect to early or other transient portions of the received signal to equivalent measurements which might have been made using BUA techniques under ideal conditions and to quote the results in terms of a BUA-equivalent, since empirical data relate BUA values to bone condition.

For clinical utility, measured and quoted characteristics must be highly reproducible both across population samples and from measurement to measurement within an individual, whether the measurements are made with one or more than one measurement unit.

In order to monitor the reliability and repeatability of the measurements, standards of various sorts have been provided to simulate the attenuation properties of bone, namely preferential attenuation of higher frequencies. One type of standard requires fabrication of a model heel structure, such as an epoxy-resin phantom, sometimes filled with particles of another material such as tungsten powder or glass beads, and sometimes temperature-regulated. These standards are known to suffer from lack of repeatability in production and application. Another type of standard known in the art is an electronic standard which simulates the spectral effect of an attenuating bone, but fails to account for mechanical aspects of the overall system, such as the transducer sensitivity to contact effects.

SUMMARY OF THE INVENTION

In a preferred embodiment, the invention provides a method for estimating a value corresponding to a broadband ultrasound attenuation of a bone. The method has a first step of providing an apparatus that has an acoustic transceiver with a pair of transducers in spaced relationship with respect to the bone, wherein a first transducer of the pair is coupled to a signal generator so as to provide an acoustic pulse having energy distributed over a frequency range and a second transducer of the pair receives an acoustic signal resulting from propagation of the acoustic pulse along a path that includes the member. The apparatus also has a signal processor, in communication with the second transducer, for providing an acoustic measure having a value, the measure being indicative of at least one of spectral or temporal components of a portion, up to the whole amount thereof, of the signal received by the second transducer. Subsequent steps of the method provided by an embodiment of the invention include measuring a first wave form $h_{subject}(t)$ resulting from use of the apparatus with the member and a second waveform $h_{cal}(t)$ resulting from use of the apparatus with a calibration medium, and deriving the value of the acoustic measure value from $h_{subject}(t)$. For any value of BUA, a filter $F_m$ is defined such that the frequency response of $F_m$ is log-linear with slope, corresponding substantially to BUA. The value of m such that the acoustic measure value computed from the waveform resulting from the application of filter $F_m$ to the second waveform $h_{cal}(t)$ matches that derived from $h_{subject}(t)$ is then determined.

Determination of the value of m satisfying the above condition may be performed on a case by case basis, or, preferably, by determining the relationship between the acoustic measure and m for a large enough set of valueds of m so that either a lookup table or an approximate functional relationship, such as a polynomial relationship, may be used.

The value of BUA derived in accordance with embodiments of the present invention achieves the calibration of a particular device since those aspects of the device that contribute to variations in $h_{subject}(t)$ are also present in $h_{cal}(t)$.

In accordance with an alternate embodiment of the invention, the transfer function $F_m$ may have the form $F_m(f) = Ae^{mf}e^{j\phi(f)} \cdot W(f)$, where A is a constant, $\phi(f)$ is a specified phase transfer function, and W(f) is a specified window function.

BRIEF DESCRIPTION OF THE DRAWINGS

The invention will be more readily understood by reference to the following drawings, taken with the accompanying detailed description, in which.

DETAILED DESCRIPTION OF SPECIFIC EMBODIMENTS

In U.S. Pat. No. 5,720,290 ("the Buhler Patent"), for an invention entitled "Apparatus and Method for Acoustic Analysis of Bone Using Optimized Functions of Spectral and Temporal Signal Components", a copy of which is attached hereto and incorporated herein by reference as Exhibit A, there is disclosed a system with which the present invention may be employed.

General Arrangements, Signal Generation, and Signal Processing

Figure 1:
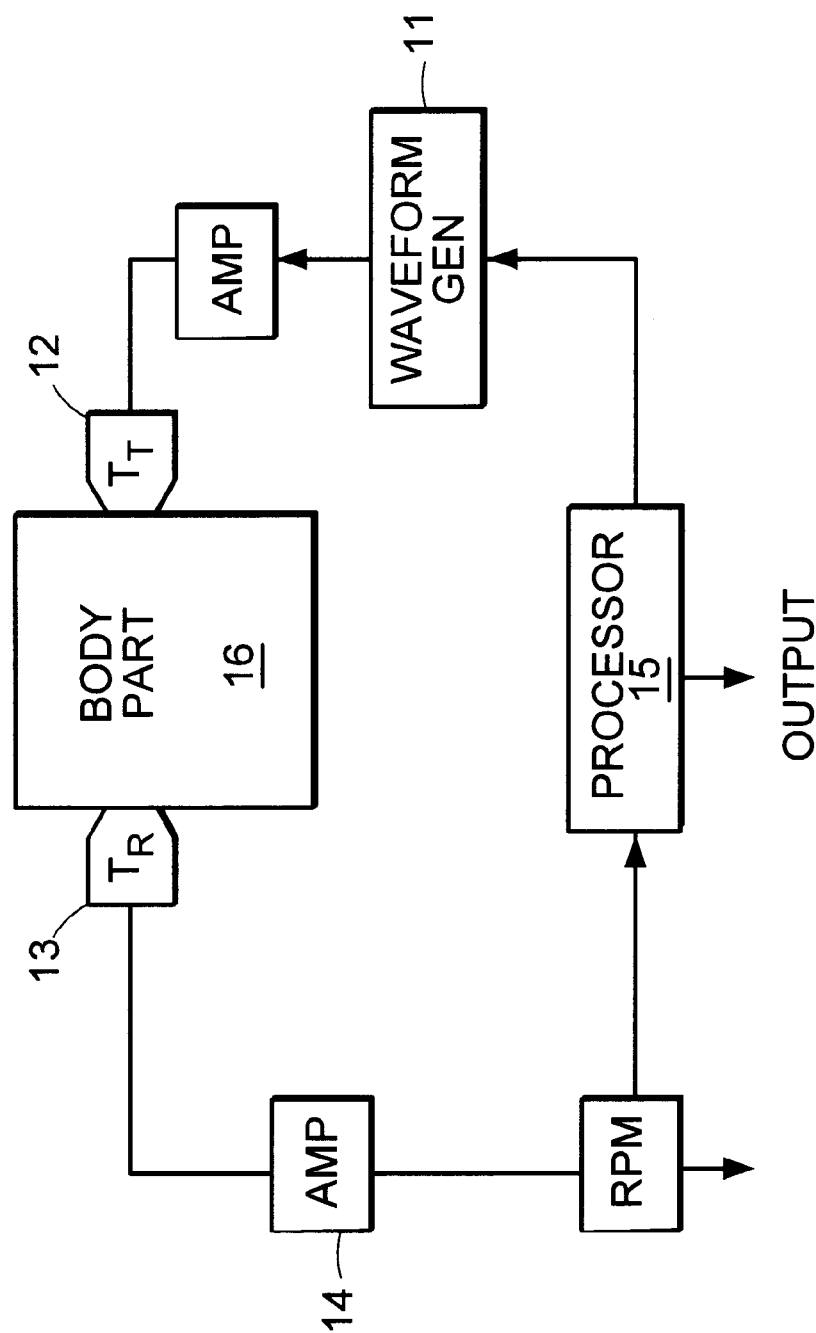
FIG. 1 is a diagram showing in general the components for a system for use in accordance with a preferred embodiment of the invention.

FIG. 1 is a diagram showing in general the components for a system of the type described in the Buhler patent and that may be used in accordance with a preferred embodiment of the present invention. In this system, a waveform is generated by waveform generator 11, and delivered to transmitting transducer $T_T$, item 12. Transducer $T_T$ is acoustically coupled to body part 16 of a subject and produces an acoustic wave that is propagated into body part 16 and in particular into a bone within the body part. The transducer $T_R$, item 13, is also acoustically coupled to body part 16 and receives a signal resulting from the effects, among other things, of propagation of the acoustic wave through the bone and the body part. Any components for transmitting and receiving an acoustic signal via a body part are referred to collectively as an "acoustic transceiver" in this description and in the appended claims. The output of the transducer $T_R$ is amplified by amplifier 14 and processed by processor 15. Processor 15 analyzes the output of the transducer $T_R$, and may make a determination reflective of the condition of the bone, and provides an output.

Figure 2:
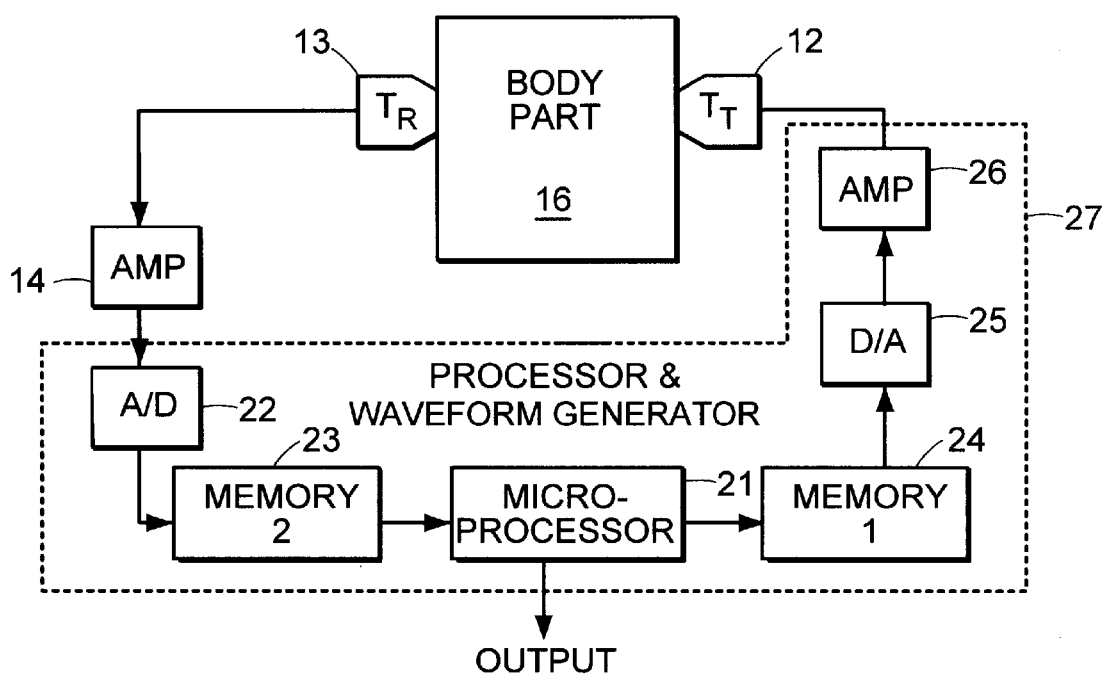
FIG. 2 is a diagram showing an implementation of the system of FIG. 1.

FIG. 2 is a diagram showing an implementation of the system of FIG. 1. The body part may be, for example, the region proximate to the calcaneus. While the elements of FIG. 1 may be implemented in analog components, in a manner known in the art, it is convenient to use a digital implementation. Accordingly, processor 15 and waveform generator 11 may be realized in a unit 27 including a microprocessor 21 that controls both processing of the output from the transducer $T_R$ and the generation of the waveform used for exciting transducer $T_T$. This waveform is stored in digitized form in memory 1, item 24, and under control of microprocessor 21 is run through digital-to-analog converter 25 before being provided to amplifier 26 and the transducer $T_T$. Similarly, the output of receiving transducer $T_R$ is fed from amplifier 14 to analog-to-digital converter 22 and this digitized output is stored in memory 2, item 23. The stored output is then processed by microprocessor 21, which provides a data output indicating the condition of the bone.

In further embodiments of the system, the embodiments of FIG. 2 (or a wholly or partially analog implementation of FIG. 1) are used to process the stored output of $T_R$ in accordance with any one or more of a variety of procedures to provide a data output indicating the condition of the bone. In accordance with some embodiments, the data output indicating bone condition includes a number, which we call the "Ultrasonic Bone Index" (UBI). Each different procedure we employ can lead to a different UBI, and the various UBI types are identified by a numerical suffix, for example, UBI-2, UBI-3, etc. The procedures for UBI-2 through UBI-8 are described in detail in the Buhler Patent. In connection with the general signal processing techniques utilized (but not their specific utilization in the context of ultrasonic bone testing), the following references are pertinent: Boualem Boashash, ed., Time-Frequency Signal Analysis (Wiley, 1992)(especially pertinent to instantaneous frequency analysis; see especially ch. 2, pages 43–73) and Richard Shiavi, Introduction to Applied Statistical Signal Analysis (Irwin, 1991)(especially pertinent to Burg Spectral Estimation; see especially pages 369–373). These texts are hereby incorporated herein by reference.

The procedures take advantage of the fact that relatively nonporous and connective bone, on the one hand, and relatively porous and non-connective bone, on the other hand, respond differently to ultrasound inputs. The various UBIs described in the Buhler Patent are relevant to the present invention and are described below.

UBI-2. In accordance with UBI-2, the stored output of TR is run through a discrete Fourier transform. A weighted linear sum of the logarithm of resulting frequency components is then computed; this sum is UBI-2. The weights are chosen to minimize differences among successive measurements taken of the same individual and to maximize differences in measurements taken of different individuals, so that the function acts as a discriminant in determining the extent of non-connectivity and porosity of bone.

UBI-3. The UBI-3 procedure utilizes the Hilbert envelope of the stored output of TR; the Hilbert envelope provides a measure of the energy content of the received waveform as a function of time. The greater preponderance of low frequency signals in the received waveform associated with healthy bone causes it to have a longer duration than in the received waveform associated with relatively porous bone. Accordingly, in accordance with UBI-3, the Hilbert envelope is examined for energy duration.

UBI-4. The UBI-4 procedure utilizes an autoregressive moving average (ARMA) spectral estimation function of the stored output TR. In one embodiment, UBI-4 uses the Burg spectral estimation function of the stored output of TR; the Burg function provides a plot estimating power versus frequency of the received waveform. The shape of the plot is a discriminant between healthy and relatively porous bone. UBI-4 is an estimate of the slope (in dB/MHZ) of the log (sdf) vs. f function. Generally the more steeply negative the slope, the healthier the bone. UBI-4b is an estimate of the slope made by reference solely to two points on the plot, the first occurring at the first peak, and the second occurring 400 kHz higher in frequency.

UBI-5. The UBI-5 procedure utilizes a measure related to the instantaneous frequency during the early portion of the received waveform. One embodiment utilizes the Hilbert frequency function. The early portion of the received waveform may be more representative of the body part, and, particularly, of the bone, under analysis in that it is not contaminated by acoustic transmission between the transmitting and receiving transducers via multiple paths. Analysis based on the early portion of the received waveform is discussed with reference to FIGS. 4A–B, FIGS. 5A–B, and FIGS. 6A–B. FIG. 24 As taught, for example, by Boashash, a signal may be represented generally in the form:

$$f(t)=a(t)e^{i\phi(t)} \qquad (1)$$

It is well known in the art that a(t) represents the envelope of the signal, and that $\phi(t)$ is the frequency function of the signal. In particular, where the decomposition of the functional behavior of the signal is made into the form of Eqn. (1) using the Hilbert transform (Boashash, at page 26), such as is appropriate where the signal predominantly tracks the central frequency of the excitation source, then the envelope, a(t), may be referred to as the Hilbert envelope and the frequency function may be referred to as the Hilbert frequency function. Both the envelope and frequency function vary as a function of time, due both to the transient nature of the excitation and the nature of the bone response, and their values, for the respective cases of diseased and healthy bone, are represented by numerals 242 and 243 in FIG. 4A and numerals 262 and 263 in FIG. 6A. For healthy bone, during the early portion (3 or 4 microseconds) of the received waveform, there is little variability and the dominant frequency is relatively low. For relatively porous bone, there is considerable variability and the dominant frequency is relatively high. The variability can be quantified according to any of a variety of methods well-known in the art. As an alternative, or in addition, to measuring the variability of the Hilbert frequency function with time, it is possible to determine the dominant frequency in a prescribed early subsection of the received burst; bad bone has a dramatically higher dominant frequency in this region. We refer to the dominant frequency and period during this time interval as the "Dominant Early Frequency" and "Dominant Early Period," respectively. One way of making this frequency or period determination is to calculate the Hilbert function in this region and then determine the average slope of the Hilbert phase vs. time plot over the interval. Alternatively, a measure of the dominant frequency in this region can be estimated directly from sample wave form data with good success. The UBI-5c index is an estimation of the period utilizing two points lying on each side of the first substantial peak. The two points in this embodiment are determined as the locations (the "inflection points") where the second derivative with respect to time is zero. The half-period is estimated as the duration between the intercepts of tangents to the curve at these two points. The UBI-5c value is the corresponding full period in microseconds.

The UBI-5d index corresponds to twice the value of the separation, in microseconds, between the first and the second substantial peaks. It is noted that the period of a sinusoid or a near-sinusoidal waveform may be determined from the slope of the waveform at the zerocrossing, scaled according to the amplitude of the waveform. A corresponding index is provided by UBI-5f, which is defined as $(2\pi A)/(dy/dt)$, where A is the peak-to-trough amplitude between the first and second substantial peaks, and dy/dt is the slope of the waveform at the zero-crossing between these peaks.

Alternate embodiments employ other measures of the early dominant frequency, all of which are within the scope of the present invention.

UBI-6. The UBI-6 procedure utilizes the short-time Fourier transform of the stored output of $T_R$ to examine in more detail than with the Hilbert transform the varying spectral content of the received waveform over time. A frequency index may be computed in a fashion analogous UBI-2. The temporal variation of this index may be used to compute a different index in a fashion analogous to UBI-5.

UBI-7. The UBI-7 procedure utilizes the Fourier transform of the stored output of $T_R$ to produce data permitting a plot of phase versus frequency; the slope of this plot is a measure of velocity (as a function of frequency). The variation of velocity (or its time domain counterpart, group delay) with frequency is dispersion, which can be quantified according to any of a variety of methods. In relatively porous bone, there is relatively little dispersion; in relatively nonporous bone, there is relatively more dispersion.

UBI-8. The UBI-8 procedure is premised on the recognition that bad bone produces a broad band signature, whereas good bone tends to pass relatively low frequencies more selectively. Accordingly, UBI-8 involves the determination of (i) "narrow-band energy," which, for the purposes of this description and the following claims, is the energy associated with 100 kHz of spectrum surrounding the low-frequency spectral peak, and (ii) "broad-band energy," which, for the purposes of this description and the following claims, is the energy associated with the full spectrum of 0–1000 kHz. UBI-8 is the normalized ratio of narrow-band energy to broad-band energy.

As described in the Buhler Patent, the foregoing UBIs are merely illustrative; other UBIs or combinations of UBIs may be utilized.

Spatial plots of the various measures of bone integrity, such as the foregoing UBIs, or others, may be obtained and displayed, as described in the Prior Application.

Spatial mapping may be achieved by any means of deriving ultrasound diagnostic information at a plurality of positions with respect to the bone of the subject. These may include, without limitation, scanning the acoustic transceiver either mechanically or electronically with respect to the bone. Spatial mapping, in accordance with various embodiments of the present invention, may be employed advantageously for a variety of purposes, including without limitation:

(a) defining one or more 'regions of interest' with respect to definable features of the bone of the subject, such as the edge or edges of the bone, which regions are of particular diagnostic utility;

(b) defining one or more 'regions of interest' with respect to definable features of the topology of the diagnostic measure itself, thus, for example, a specified region surrounding a minimum with respect to a particular UBI parameter, where such a region is known to be of particular diagnostic utility;

(c) determining the on-bone/off-bone transition, i.e., the edge of the bone, for use in defining regions of particular diagnostic utility; and (d) employing topological signatures or geometrical features of the spatial map itself as one or more diagnostic measures. Thus, for example, the curvature of a particular UBI field, as a spatial function, may be employed, in accordance with an embodiment of the present invention, for diagnostic purposes.

Figure 7:
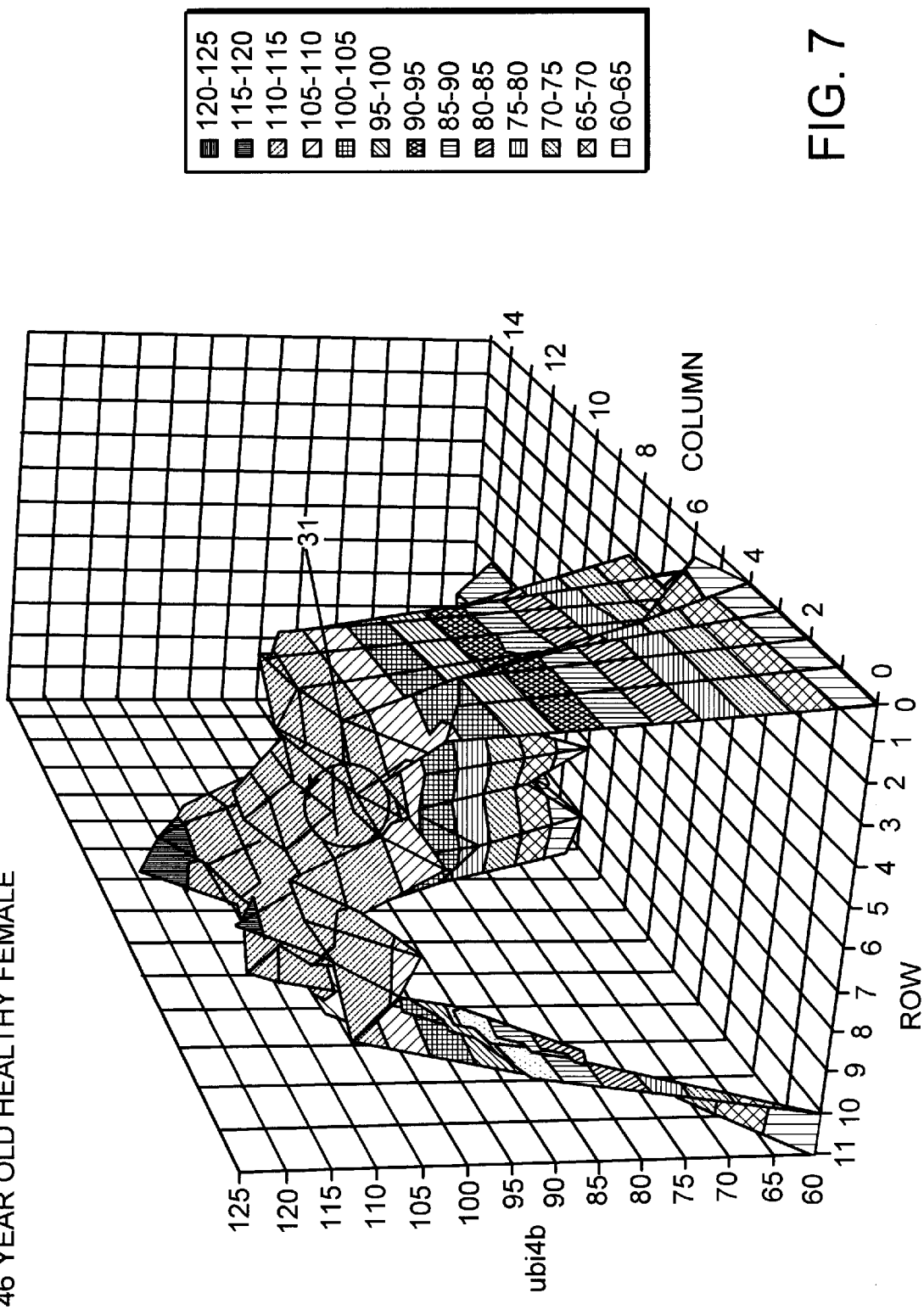
FIGS. 7 and 8 are surface plots of UBI-4b and UBI-5c respectively over a two-dimensional region of the calcaneus of a 46-year old healthy female.
Figure 8:
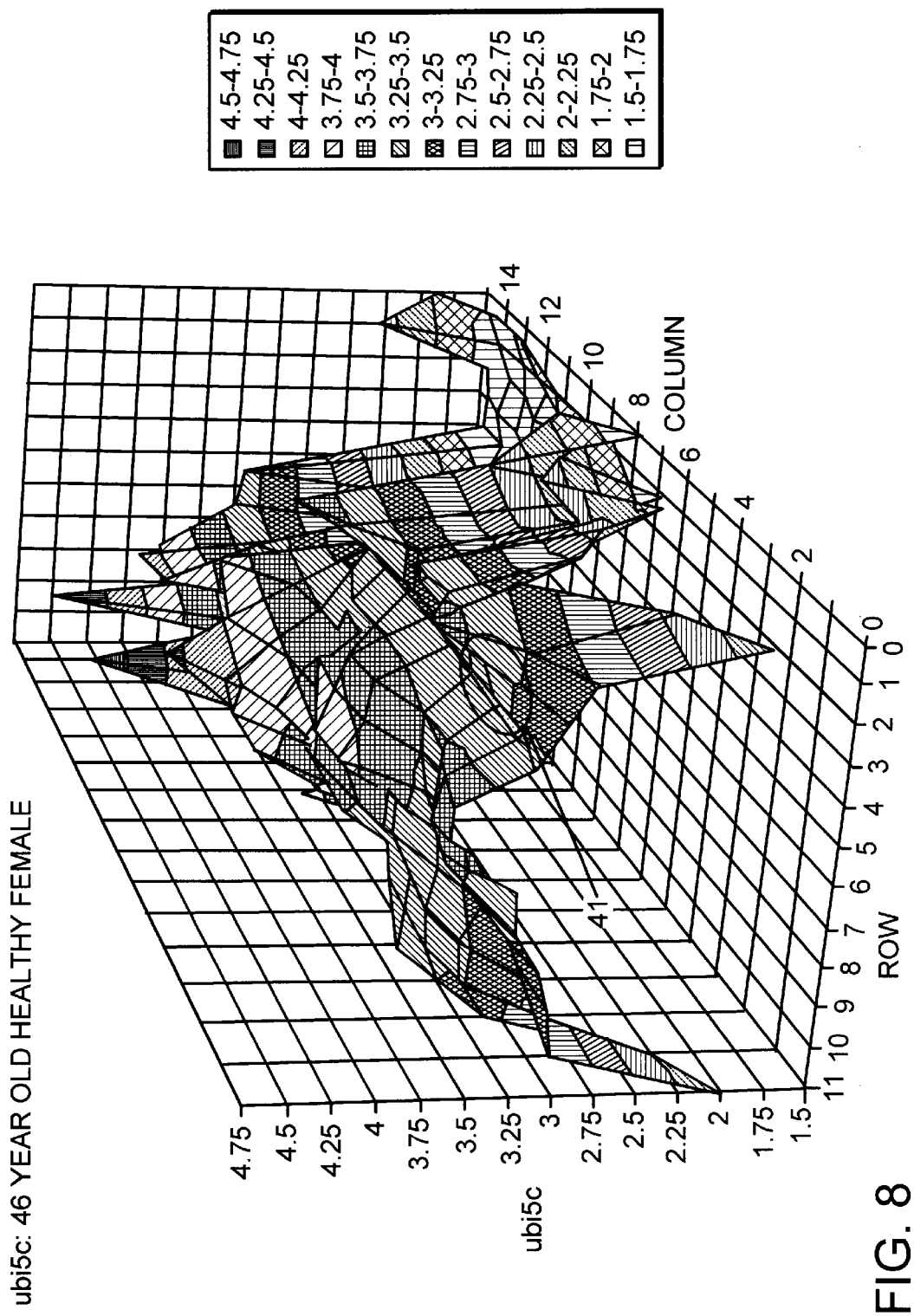

FIGS. 7 and 8 are three-dimensional surface plots of UBI-4b and UBI-5c respectively over a two-dimensional region of the calcaneus of a 46-year old healthy female. In these plots, the axis marked "Column" on the right approximates the heel-to-toe axis, with the heelmost position (i.e., toward the back of the heel) lying at the origin. (On this and subsequent plots, the region presented may not necessarily include the near edge of the calcaneus.) The axis marked "Row" is in a direction perpendicular to the "Column" axis, again with the heelmost position (i.e., toward the bottom surface of the heel) at the origin. These two axes are used identify coordinates associated with the transducer pair $T_T$ and $T_R$ of FIGS. 1 and 2. The transducer pair may be in a fixed disposition relative to each other, as in cradle 166 of FIG. 16 of the Buhler Patent, so that an ultrasound pulse is transmitted from transducer $T_T$ along a path through the calcaneus to transducer $T_R$ and processed in the manner as described in the Buhler Patent. The pertinent UBI is determined with the two transducers in a given location. The transducers are then moved relative to the bone to a series of different locations so as to permit the determination of a collection of UBI values over an entire region of interest. (However, the particular manner in which the transducers are mounted and moved is not a part of the present invention.) The two axes (Column and Row) therefore identify the position of the transducer pair relative to the subject's foot. Finally, the vertical axis shows the pertinent UBI value determined for each location.

The methods and apparatus described herein may advantageously be applied, within the scope of the present invention, for providing an earlier indication of the deterioration of bone quality than would be provided by the value alone of a bone quality measure at a specified location. All of the foregoing techniques, alone or in combination, may be used to determine a propensity for a subject to change of porosity of bone, applying methods of longitudinal clinical study known to persons of ordinary skill in the art.

Estimation of BUA from a UBI Measure

We next discuss an approach permitting the determination of an estimate of BUA, or, alternatively, a BUA equivalent, from a UBI measure, such as UBI-5f. While the method described hereinafter provides an estimate of BUA, this estimate is intended to be of clinical utility to a user and there is no implication that the UBI measures are subject to the same limitations and inherent deficiencies of the BUA with respect to specificity and sensitivity.

Figure 9:
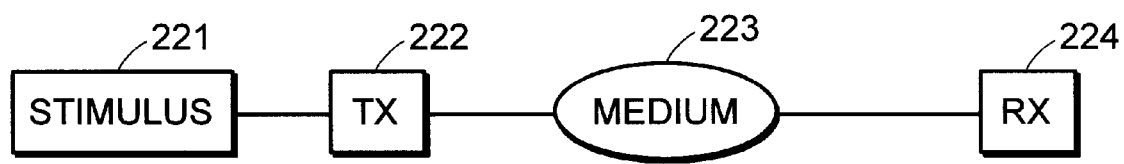
FIG. 9 is a schematic model of the ultrasonic analysis system for purposes of estimating other measures of bone integrity from one or more UBI measures in accordance with an embodiment of the present invention.

The system, in accordance with the present invention, may, in general, be modeled as shown in FIG. 9. In this figure, Tx (item 222) represents the transmitter (electronics plus transducer); Rx (item 224) represents the receiver (electronics plus transducer). Medium (item 223) is the test material or subject between the transducers. Stimulus (item 221) is the excitation function, often impulse-like. For purposes of this description, the stimulus may be considered as a part of the transmitter function. The response h(t), as a function of time t, of a system such as shown in FIG. 9 can be written as $$h(t)=h_{Tx}(t)*h_{Medium}(t)*h_{Rx}(t) \quad (1)$$

where the asterisk [*] represents convolution, and $h_{Tx}(t)$, $h_{Medium}(t)$, and $h_{Rx}(t)$ are the separate impulse responses associated respectively with the transmitter, Medium, and receiver.

In accordance with an embodiment of the invention, the transmitter output may be applied to either of two types of media:

(1) a calibration medium, such as water or other liquid or solid medium that exhibits, at most, low levels of frequency dependent attenuation and velocity dispersion; and (2) a test medium, such as the heel of a human subject.

In the respective cases, the signals measured may be expressed as calibration signals $h_{cal}$ and test signals $h_{test}$, which, in view of equation (1), give us:

$$h_{cal}(t)=h_{Tx}(t)*h_{cal\ medium}(t)*h_{Rx}(t) \quad (2)$$

$$h_{test}(t)=h_{Tx}(t)*h_{test\ medium}(t)*h_{Rx}(t) \quad (3)$$

When the calibration medium is water or other acoustically neutral (i.e., lossless and dispersionless) or near-neutral medium, $h_{cal}(t) \approx \delta(t-t_0)$; that is, the signal undergoes a simple time delay (by time $t_0$) without distortion.

Note that the effects of contact between transducer and the test medium are implicitly included in $h_{test}$, and those for the cell are implicitly included in $h_{cal\ medium}$. To first order, these effects may be neglected.

A procedure in accordance with an embodiment of the invention is now described for converting a UBI measurement to a BUA value. Such conversion may be advantageous for purposes of providing clinical data for comparison with clinical data correlating BUA values with bone porosity. Thus, for example, clinical results of testing a subject may be expressed, if so desired, in terms of BUA values In addition, the procedures given for converting to BUA accomplish the calibration of the equipment.

Figure 3A:
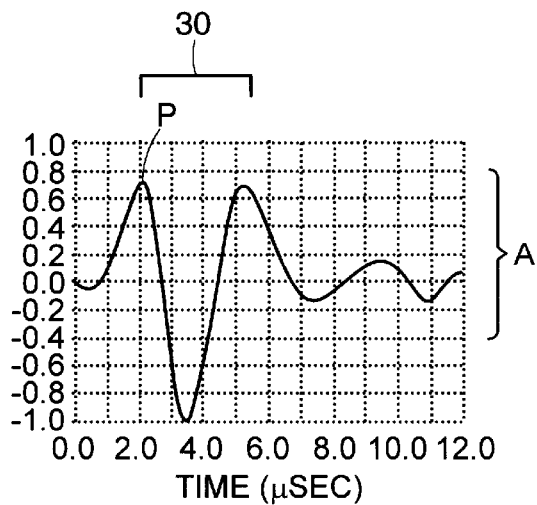
FIGS. 3A–C show a comparison of typical waveform signatures received in cases of healthy bone, osteoporotic bone, and water calibration.
Figure 3B:
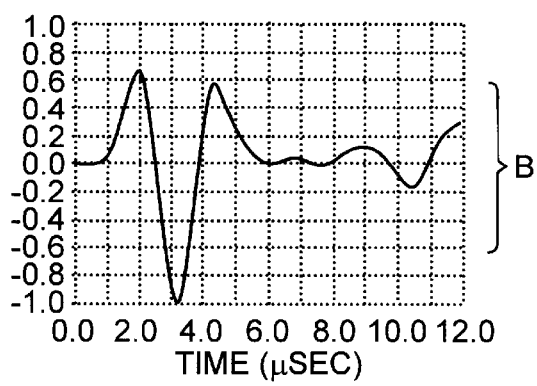
Figure 3C:
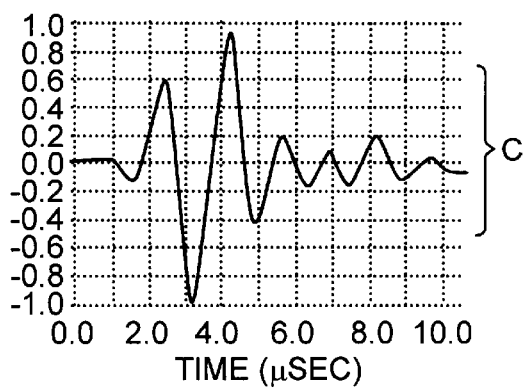
Figure 4A:
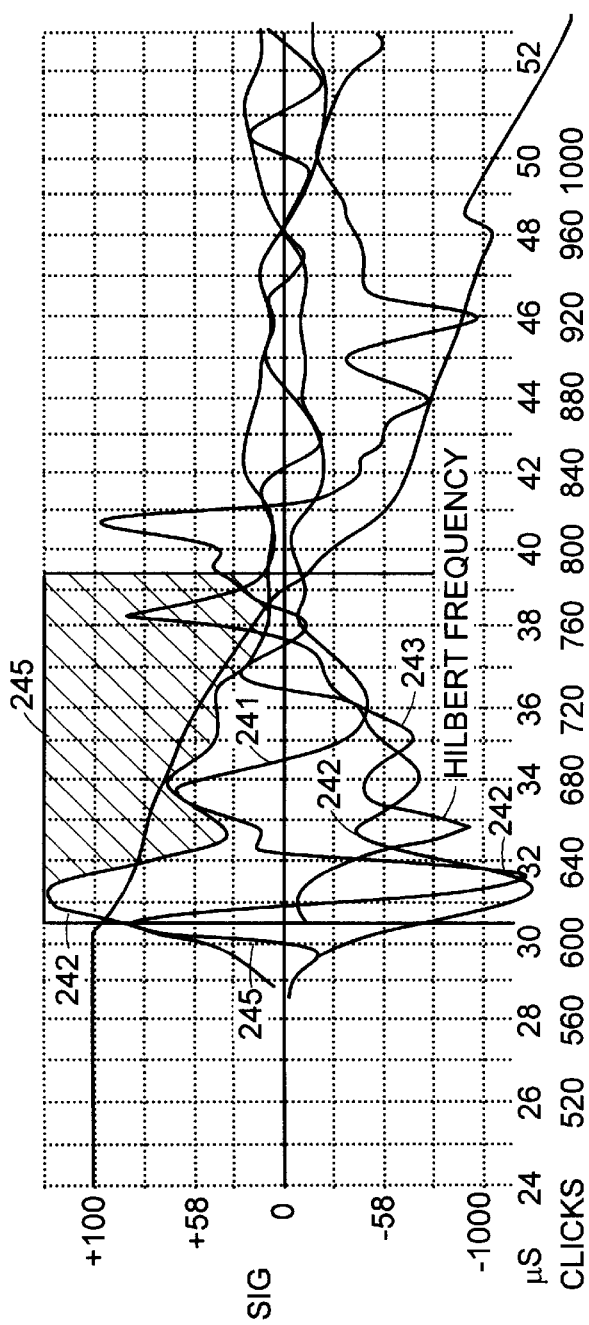
FIG. 4A provides a plot showing the stored output of transducer $T_R$ of FIG. 1 in response to an excitation waveform, generated by the system of FIG. 1 and transmitted through a bone having substantial porosity, as well as plots pertinent to calculation of UBIs in accordance with a preferred embodiment of the invention.
Figure 4B:
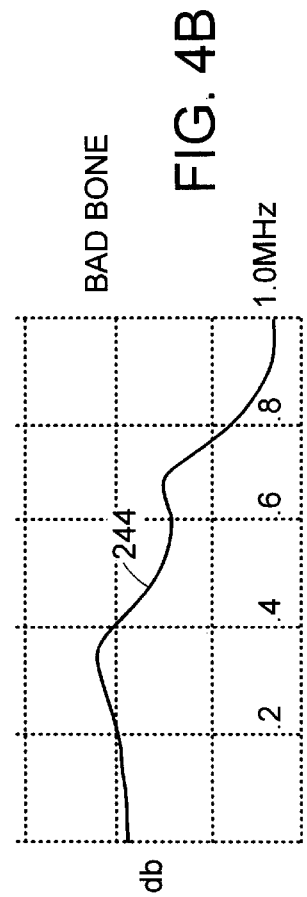
FIG. 4B provides a plot of the Burg spectral estimation function associated with plots of FIG. 4A.
Figure 5A:
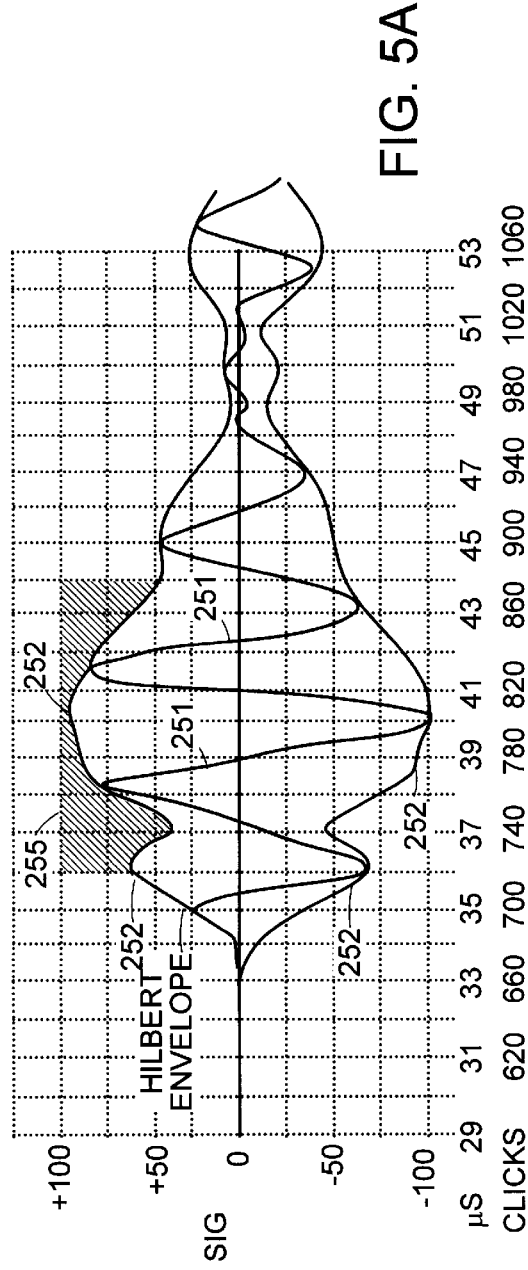
FIG. 5A provides a plot showing the stored output of transducer $T_R$ of FIG. 1 in response to an excitation waveform, generated by the system of FIG. 1 and transmitted through a bone of low-normal quality, as well as plots pertinent to calculation of UBIs in accordance with a preferred embodiment of the invention.
Figure 5B:
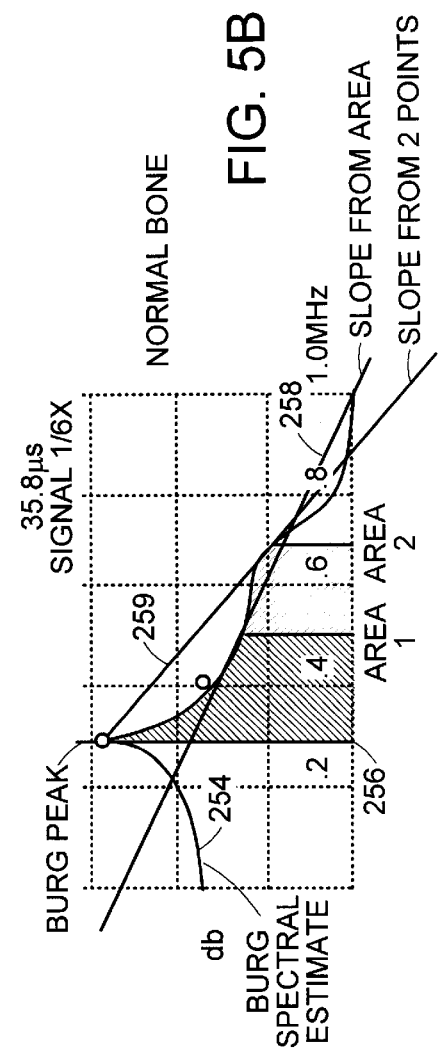
FIG. 5B provides a plot of the Burg spectral estimation function associated with plots of FIG. 5A.
Figure 6A:
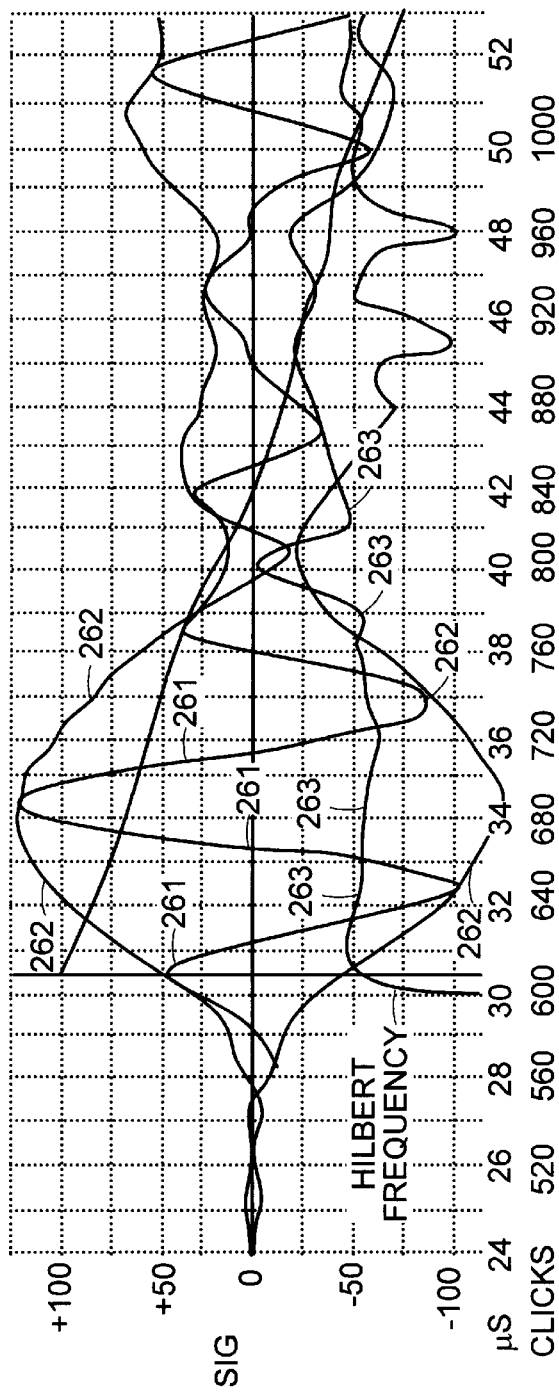
FIG. 6A provides a plot showing the stored output of transducer $T_R$ of FIG. 1 in response to an excitation waveform, generated by the system of FIG. 1 and transmitted through an exceptionally healthy bone, as well as plots pertinent to calculation of UBIs in accordance with a preferred embodiment of the invention.
Figure 6B:
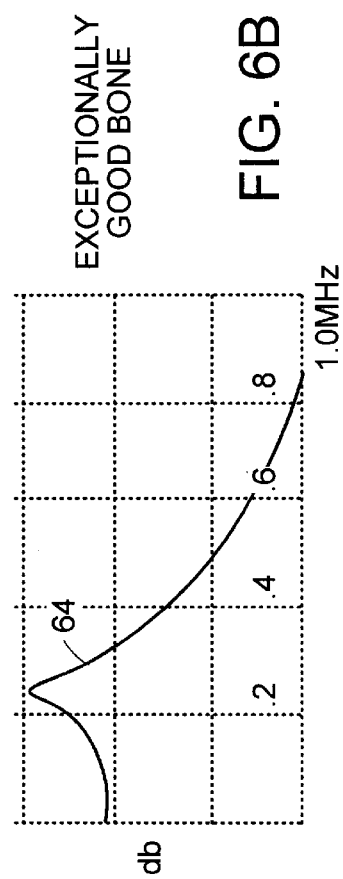
FIG. 6B provides a plot of the Burg spectral estimation function associated with plots of FIG. 6A.

Referring now to FIGS. 3A–C, wave form A illustrates a signal that might be obtained from receiver Rx using a healthy bone as part of the Medium. The approximate period 30 of the first cycle or two is ~3–4 microseconds (and ~2–2.5 microseconds for unhealthy bone). Wave form B illustrates a corresponding signal using an osteoporotic bone, showing a shorter first cycle than in wave form A. Wave form C illustrates a typical water calibration signal. The period of the first few cycles is 1.5–2 microseconds. The measure UBI-5f is derived by estimating the frequency (and period) near the first positive peak (P in FIG. 3A).

A BUA estimated value corresponding to the signal A and its UBI-5f value may be derived as follows. First, assume a hypothetical family of filters providing responses $h_{filter}(t)$ that are defined by a transfer function $F_m$ having the form $$F_m(f)=Ae^{mf}e^{i\phi} \cdot W(f) \quad (4)$$

where: m represents the (negative) slope of a log-linear amplitude function, and, more particularly, m=—(BUA*ln 10)/20, where ln is the natural logarithm;

A is a constant;

φ(f) is a phase transfer function; and

W(f) is a (multiplicative) window function that may be present if necessary to adjust for signal processing artifacts (such as ringing).

The function $h_{filter}(t)$ may be determined from $F_m(f)$ through a standard Inverse Fourier Transform.

The discussion presented herein may be generalized to other transforms, as known to persons skilled in the art of signal processing, and such generalizations are within the scope of the invention as claimed in the appended claims.

The idea is to find the relationship between BUA and any specified acoustic measure such as UBI-5f, by finding, for multiple values of BUA, the function $h_{filter\ system}(t)$, where $$h_{filter\ system}(t)=h_{Tx}(t)*h_{filter}(t)*h_{Rx}(t) \quad (5)$$

and calculating the acoustic measure corresponding to this function $h_{filter\ system}(t)$. By repeating this process for a sufficient number of values of BUA, a correspondence may be derived between BUA and the acoustic measure that can be expressed either in a lookup table or in an approximate functional relationship such as a polynomial function. The BUA value for a given $h_{subject}(t)$ is then determined by applying either the functional relationship of the lookup table to the value of the acoustic measure computed from $h_{subject}(t)$. For example, the relationship between any of the parameters UBI-5b, UBI-5c, UBI-5d, and UBI-5f has been found to be substantially linear, with a linear slope and an intercept that may be derived for a given instrument by the fitting procedure described above. The conversion between the given UBI value and BUA may then be accomplished simply by applying the slope and intercept that the define the corresponding relationship.

Alternatively, the BUA value corresponding to any single measurement $h_{subject}(t)$ may be derived by finding the value of m such that $h_{filter\ system}(t)=h_{Tx}(t)*h_{filter}(t)*h_{Rx}(t)$ provides the best match to $h_{subject}(t)$ over some prescribed interval of time. In this case, the other parameters in Eqn. 4 must also be found, for example, using nonlinear least squares techniques, to give the best overall fit.

Phase transfer function φ(f) may be taken as a constant. This is equivalent to assuming there is no dispersion and that the zero of time is redefined so as to remove the remaining linear phase function associated with a fixed delay from Tx to Rx. Alternatively, φ(f) may be taken as a quadratic function whose second order term will correspond to the amount of dispersion in the subject medium. Finally, a minimum phase filter may be specified, as is frequently chosen for modeling the phase of a physical system when the phase is not independently known. Similarly, one may initially set W(f)=1. In the event of interference from deleterious artifacts, one may thereafter establish a suitable window W(f) to reduce the effect of such artifacts, as known to persons skilled in the art of signal processing.

Note that since $h_{cal\ medium}=\delta(t-t_0)$ is an excellent approximation for calibration with water or other nearly neutral acoustic medium, $h_{filtered\ system}(t)=h_{cal}(t)*h_{filter}(t)$ to the same approximation. This method assumes that the calibration medium, like water, has substantially frequency independent attenuation and is substantially free of dispersion in a frequency range of interest. However, the method can be readily modified utilizing the relationships outlined above to deal with other calibration media having other acoustic properties.

It has been found that insufficient accuracy of the assumptions regarding negligibility of contact effects and acoustic neutrality of the medium may result in overestimation of the differences between different instruments when the above methods are applied. Compensation for overestimation or other effects is provided, in accordance with an embodiment of the present invention, by introduction of an empirical multiplicative factor a that describes the fraction of the derived difference that will be compensated in practice. Thus, if two instruments are predicted to differ by N BUA units, the difference, after calibration of the instruments, will be αN.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for estimating a value m corresponding to a broadband ultrasound attenuation of a member, the method comprising:
   (a) providing an apparatus, the apparatus comprising:
      (i) an acoustic transceiver having a pair of transducers in spaced relationship with respect to the member, wherein a first transducer of the pair is coupled to a signal generator so as to provide an acoustic pulse having energy distributed over a frequency range and a second transducer of the pair receives an acoustic signal resulting from propagation of the acoustic pulse along a path that includes the member;
      (ii) a signal processor, in communication with the second transducer, for providing an acoustic measure having a value, the measure being indicative of at least one of spectral or temporal components of a portion, up to the whole amount thereof, of the signal received by the second transducer;
   (b) measuring a first wave form $h_{subject}(t)$ resulting from use of the apparatus with the member and a second waveform $h_{cal}(t)$ resulting from use of the apparatus with a calibration medium;
   (c) deriving the value of the acoustic measure value from $h_{subject}(t)$;
   (d) finding $h_{filter\ system}(t)=h_{filter}(t)*h_{cal}(t)$ for a plurality of values of m;
   (e) associating for each value of m a value of the acoustic measure yielding a substantially equal $h_{filter\ system}(t)$; and
   (f) associating the value m with the value of the acoustic measure associated with the wave form $h_{subject}(t)$.

2. A method according to claim 1, wherein $h_{filter}(t)$ is a Fourier transform of a transfer function $F_m$, the transfer function having a form:

$$F_m(f)=Ae^{mf}e^{i\phi(f)} \cdot W(f)$$

A being an arbitrary constant;

φ(f) being a specified phase transfer function; and

W(f) is a specified window function.

3. A method according to claim 2, wherein the window function is identical to unity.

4. A method according to claim 1, wherein the calibration medium has substantially frequency independent attenuation over a specified frequency range.

5. A method according to claim 1, wherein the calibration medium is water.

6. A method according to claim 1, further comprising the step of associating the value of the transient acoustic measure with a log-linear broadband ultrasound attenuation (BUA) value corresponding to the value m.

7. A method according to claim 1, further including the step of compiling a table of related values of the acoustic measure and BUA values.

8. A method according to claim 1, further including the step of fitting a functional relation between the values of the acoustic measure and the BUA values.

9. A method according to claim 8, wherein the functional relation is a polynomial relation.

10. A method according to claim 1, wherein the acoustic measure is a transient acoustic measure.

11. A method according to claim 1, wherein the acoustic measure is an ultrasonic bone index.

* * * * *